United States Patent [19]

Becker et al.

[11] 4,023,709
[45] May 17, 1977

[54] APPARATUS FOR DOSING A CONSTANT QUANTITY OF FLUID INTO AN ANALYSIS DEVICE

[75] Inventors: Wolf-Jürgen Becker; Werner Magerkorth, both of Leverkusen, Germany

[73] Assignee: Bayer Aktiengesellschaft, Leverkusen, Germany

[22] Filed: July 8, 1976

[21] Appl. No.: 703,400

[30] Foreign Application Priority Data

July 31, 1975 Germany .......................... 2534260

[52] U.S. Cl. .................................. 222/70; 222/318
[51] Int. Cl.² ........................................ B67D 5/08
[58] Field of Search ............ 222/70, 330, 331, 328

[56] References Cited
UNITED STATES PATENTS 3,885,739  5/1975  Tuttle ............................. 222/331 X

*Primary Examiner*—Stanley H. Tollberg
*Assistant Examiner*—Hadd Lane
*Attorney, Agent, or Firm*—Burgess, Dinklage & Sprung

[57] ABSTRACT

In an apparatus for the discontinuous dosing of a constant quantity of fluid into an analysis device, the fluid feed system is connected by means of a three-way valve on the one hand via the dosing valve and a shut off valve arranged downstream and on the other hand via a by-pass to the fluid discharge system. A compressed air source for the production of a constant air pressure is connected between the three-way valve and the dosing valve. All the components of the system are controlled by a programme control unit, so that the fluid flow through the dosing valve is temporarily interrupted by closing the shut off valve and switching over the fluid feed to the by-pass and at the same time releasing the connection of the compressed air to the dosing valve. Thereafter the compressed air source is switched off by the control unit and the interruption of the fluid flow at the dosing valve is cancelled.

2 Claims, 1 Drawing Figure

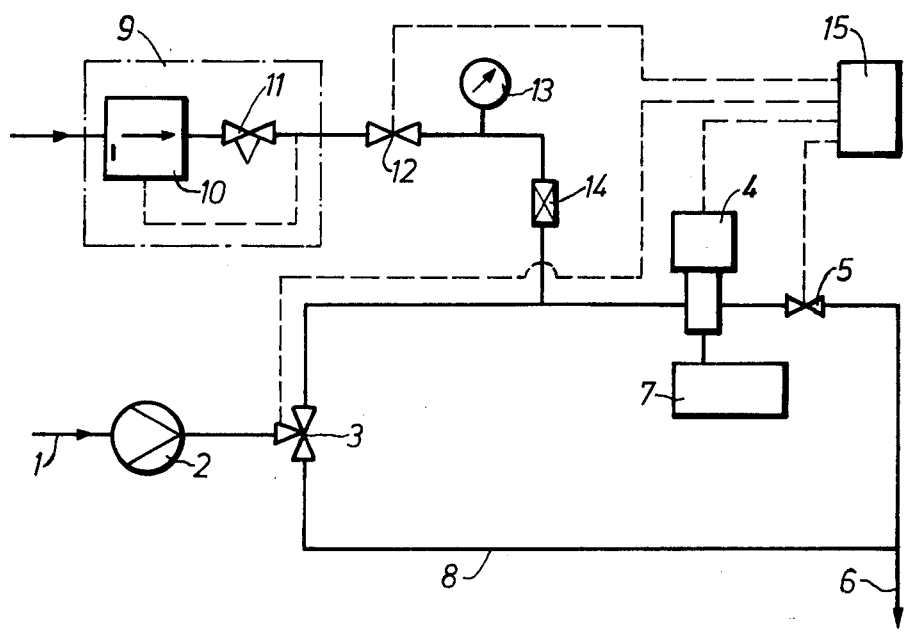

APPARATUS FOR DOSING A CONSTANT QUANTITY OF FLUID INTO AN ANALYSIS DEVICE

The invention relates to an apparatus for the discontinuous dosing of a constant quantity of fluid into an analysis device. The analysis device is provided with a fluid dosing valve, through which the fluid to be analysed flows.

In the automatic analysis of the total carbon content of fluids, a defined quanitity of fluid must be injected into a combustion furnace. A suitable injection valve is for example described in German Offenlegungsschrift No. 2,261,449. This injection valve consists of a valve needle, which for the entry of the fluid is opened for a short time. During this time a small sample of the pressurized fluid is injected into the combustion chamber where the sample is pyrolysed. The water vapour and the compounds containing carbon which are burned to form carbon dioxide are then transported to a carbon dioxide gas analysis device by means of a carrier gas and quantitatively anaylsed.

To generate a constant pressure at the fluid inlet valve, according to German Offenlegungsschrift No. 2,261,449 a pump with an equalising volume is connected in the fluid feed system to the injection valve and a pressure regulator with a regulator valve is connected in the discharge system. In this way the fluid flows continuously through the valve and the composition of the sample always corresponds to the state of the sampled fluid at that time. This is important in order to obtain information as early as possile on any change in the sample fluid. Gear pumps have proved valuable for producing a suitable supply pressure for the injection valve. The pressure regulator with regulator valve works as a throttle point and keeps the fluid over-pressure at the valve constant. The buffer volume between the valve and the pump equalises the pressure impulses originating from the pump.

This dosing method has the following disadvantages:

The volume dosed by the valve is dependent on the pressure of the sample fluid in the valve. It is therefore necessary to keep the pressure of the sample fluid very constant. This requirement cannot always be fulfilled. It has been shown that in spite of the interposed buffer volume, small pressure impulses are still transmitted from the gear pump, affecting the accuracy of dosing. Moreover it is very involved and difficult with a flowing quantity of water to maintain the water pressure constant at a dosing valve by the measurement and regulation of the pressure. In any event, a very expensive and complicated gear pump is necessary to achieve this. It would be desirable to use simpler commercial feed pumps.

The object of the invention therefore is to improve the known dosing apparatus with an injection valve, so that a very constant and reproducible dosing rate is guaranteed. This aim should be achieved with as little apparatus as posible.

According to the invention, there is provided an apparatus for the discontinuous dosing of a constant quantity of a fluid into an analysis device, comprising a dosing valve through which the fluid to be analysed flows, a three-way valve connecting an inlet for the fluid either through the dosing valve and a first shut-off valve connected downstream of the dosing valve, or through a by-pass conduit, to an outlet for the fluid, a source of compressed gas for the production of a constant gas pressure connected via a second shut-off valve to a conduit connected between the three-way valve and the first shut-off valve, and a programme control device connected to the dosing valve, the first and second shut-off valves and the three-way valve, the programme control device, when in use, during a dosing process, temporarily interrupting the fluid flow through the dosing valve by closing the first shut-off valve and switching the three-way valve to the by-pass conduit and connects the source of compressed gas to the conduit between the three-way valve and the first shut-off valve, so that the quantity of fluid contained between the three-way valve and the first shut-off valve is under the gas pressure during the dosing process, whereafter the second shut-off valve is closed and the fluid flow through the dosing valve is resumed.

The solution of the problem therefore rests on applying a constant fluid pressure for a short time only during the dosing period at the dosing valve and tying in the pressure regulation of the fluid with the pressure regulation of a gas (air).

The advantages obtained with the invention are in particular that a very constant easily reproducible fluid pressure is produced at the dosing valve and that the pumping device for the fluid to be dosed has no influence on the dosing rate. The pulsating functioning of commercial pumps no longer disrupts the dosing process. As the feed pumps, simple pumps e.g. hose pumps, membrane pumps, centrifugal pumps or gear pumps can be used.

An embodiment of the invention is illustrated in the drawing and is described in more detail in the following.

The figure shows a schematic diagram of the apparatus for producing a constant fluid pressureat the dosing valve.

During the time in which the sample fluid is not to be dosed, it is pumped from a feed 1 by means of a pump 2 via a three-way valve 3 through a dosing valve 4 and then via a two-way shut-off valve 5. Then the sample fluid is passed out into a discharge system 6. If it is desired that a sample be dosed into an analysis unit 7, the fluid flow is temporarily interrupted by the dosing valve 4 and shut-off. The three-way valve 3 swithces over for this purpose and the sample fluid flows via a by-pass 8 direct into the discharge system 6. The feed to the three-way valve 3 must close tightly in relation to the dosing valve 4. At the same time the shut-off valve 5 is closed and by means of a compressed air source 9, via a feed line connected to the conduit between the three-way valve 3 and the dosing valve 4, a constant supply pressure is exerted on the dosing valve 4. The effect of this is that during the dosing process the quantity of fluid contained in the dosing valve 4 is kept under the constant supply pressure of the compressed air source 9. The compressed air source 9 consists of a pressure regulator 10 and an adjusting valve 11, which is connected to an internal compressed air system. The gas pressure regulator 10 is a commercially available component. From a fluctuating input pressure it produces a highly constant output pressure. The output pressure from the regulator is adjusted by the adjusting valve 11. The compressed air source 9 is switched on by a shut-off valve 12. A manometer 13 for monitoring the output pressure and a check valve 14 are also incorporated in the connection pipe. The check valve 14 is intended to prevent sample fluid from entering the compressed air line. It can be dispensed with if it is certain that the shut-off valve 12 is properly sealed or can be evacuated of air.

After the dosing of a fluid sample with the dosing valve 4 the three shut-off valves 3, 5 and 12 are returned to their staring positions. This switches off the air pressure and the sample fluid flows back through the dosing valve 4 to the discharge system 6. The fluid flow through the dosing valve 4 is resumed.

The three-way valve 3, dosing valve 4, shut-off valve 5 in the dosing valve out-flow and shut-off valve 12 in the compressed air line are magnetic valves, which are electrically activated. They are controlled by the programme control unit 15 according to the above described sequence of the dosing process.

It is self-evident that instead of air for producing a constant supply pressure at the dosing valve, another gas, e.g. nitrogen, can be used. For this purpose it would only be necessry to connect a nitrogen cylinder to the pressure regulator 10.

What We Claim Is:

1. An apparatus for the discontinuous dosing of a constant quantity of a fluid into an analysis device, comprising a dosing valve through which the fluid to be analysed flows, a three-way valve connecting an inlet for the fluid either through the dosing valve and a first shut-off valve connected downstream of the dosing valve, or through a by-pass conduit, to an outlet for the fluid, a source of compressed gas for the production of a constant gas pressure connected via a second shut-off valve to a conduit connected between the three-way valve and the first shut-off valve, and a programme control device connected to the dosing valve, the first and second shut-off valves and the three-way valve, the programme control device, when in use, during a dosing process, temporarily interrupting the fluid flow through the dosing valve by closing the first shut-off valve and switching the three-way valve to the by-pass conduit and connects the source of compressed gas to the conduit between the three-way valve and the first shut-off valve, so that the quantity of fluid contained between the three-way valve and the first shut-off valve is under the gas pressure during the dosing process, whereafter the second shut-off valve is closed and the fluid flow through the dosing valve is resumed.

2. An apparatus as claimed in claimed 1, wherein the source of compressed gas comprises an air pressure regulator and an adjusting valve.

* * * * *